(12) United States Patent
Poezevara

(10) Patent No.: US 7,440,795 B2
(45) Date of Patent: Oct. 21, 2008

(54) DETECTING SLEEP DISORDERS USING AN ACTIVE IMPLANTABLE MEDICAL DEVICE

(75) Inventor: Yann Poezevara, Courcouronnes (FR)

(73) Assignee: Ela Medical S.A.S., Montrouge (FR)

( * ) Notice: Subject to any disclaimer, the term of this patent is extended or adjusted under 35 U.S.C. 154(b) by 184 days.

(21) Appl. No.: 10/742,520

(22) Filed: Dec. 19, 2003

(65) Prior Publication Data
US 2004/0176695 A1 Sep. 9, 2004

(30) Foreign Application Priority Data
Dec. 24, 2002 (FR) .................................. 02 16608

(51) Int. Cl.
*A61B 5/0402* (2006.01)
(52) U.S. Cl. .................... 600/509; 600/484; 600/510
(58) Field of Classification Search .............. 600/509, 600/519, 515, 529, 513, 483–484
See application file for complete search history.

(56) References Cited

U.S. PATENT DOCUMENTS

| 4,580,575 A * | 4/1986 | Birnbaum et al. ........... 600/484 |
| 2002/0138012 A1 * | 9/2002 | Hodges et al. .............. 600/509 |
| 2003/0153953 A1 * | 8/2003 | Park et al. .................. 607/17 |

FOREIGN PATENT DOCUMENTS

| EP | 940 155 A2 | 9/1999 |
| EP | 1 151 718 A2 | 11/2001 |
| EP | 1 151 719 A2 | 11/2001 |

* cited by examiner

*Primary Examiner*—Carl H. Layno
*Assistant Examiner*—Deborah Malamud
(74) *Attorney, Agent, or Firm*—Orrick Herrington & Sutcliffe, LLP

(57) ABSTRACT

An active medical device, in particular an implantable device such as a cardiac pacemaker, defibrillator, cardioverter, or multisite device, including a function for determining sleep disorders. This device can collect the heartbeat rhythm in at least one heart cavity, and analyze the collected rhythm so as to evaluate a value of heartbeat rate accordingly. The device can also discriminate within a collected heart rhythm the spontaneous events of sinusal origin, and to evaluate the heart rate according only to these spontaneous sinusal events, and to analyze the time variations of the aforementioned heart rate to determine the presence of a sleep respiratory disorder accordingly. This analysis can be realized through a search for episodes of bradycardia followed by episodes of tachycardia, or by determination of an index of sinusal variability that is a function of the detected variations, and comparison of this index with a predetermined threshold.

6 Claims, 2 Drawing Sheets

DETECTING SLEEP DISORDERS USING AN ACTIVE IMPLANTABLE MEDICAL DEVICE

FIELD OF THE INVENTION

The present invention relates to the diagnosis of sleep respiratory disorders, and more particularly to the diagnosis of apnea or hypopnea episodes. The invention also relates, inter alia, to diagnosing affections such as the sleep apnea syndrome (SAS), the obstructive apnea or central apnea, a pathology that is likely to involve a certain number of disorders such as diurnal hypersomnolence, heart rate disturbance, and hypertension.

BACKGROUND OF THE INVENTION

SAS can be defined by a significant recurrence of apneas or hypopneas associated with clinical symptoms. An "apnea" or "respiratory pause" is a temporary stop of the respiratory function of a duration longer than 10 seconds that occurs during a phase of sleep of the patient. A "hypopnea" is defined as a significant decrease of the minute ventilation, for example, more than 50%, compared to an average of prior minute ventilation measures, but without a stoppage of the respiratory function. The minute ventilation is the product of the amplitude by the frequency of the successive respiratory cycles.

Various techniques to detect these sleep respiratory disorders are known. Among these techniques are those that implement various types of sensors, in particular a sensor of minute ventilation, a parameter having a physiological preponderance that is obtained by an intrathoracic impedance measurement operated by an implanted device.

The measurement of the minute ventilation is carried out by an injection of pulses of a constant current having an amplitude of a few hundred microamperes at a frequency of a few hertz. The current injection can take place, for example, between two electrodes laid out in the rib cage, or between the case of the implanted medical device and an electrode, e.g., a stimulation electrode if the implanted device is a cardiac pacemaker. The measured impedance variations reproduce the variations of the thoracic volume, with peaks of impedance at the time of the inspiration when the lungs are filled with air, and a decreasing impedance at the time of the expiratory phase.

Other techniques have been proposed, based on the measure of a parameter having a physiological preponderance such as the oxygen saturation in blood. In this regard, a prolonged reduction of respiratory activity produces a correlative desaturation of oxygen. This condition can be detected by an adapted sensor, for example, placed at the end of a catheter or a probe of a cardiac pacemaker.

It was noted in practice, however, at the time of clinical studies, that a system implementing a respiratory activity sensor, recording the variations of the pulmonary volume at the thoracic level can in certain circumstances be deluded during the sleep for various reasons:
1. internal physiological reasons, for example, a body position or a movement inducing a modification of volumes and/or position of the concerned organs,
2. clinical reasons, for example, because of breathing that is exclusively abdominal in origin, or
3. external reasons, for example, because of momentary electromagnetic interference.

In these particular situations, this device detects wrongly the occurrence of an apnea or of a hypopnea, whereas the breathing is actually normal but was not diagnosed as such by the device. In the same way, an apnea or a hypopnea can cause a micro-waking up of the patient without affecting to a significant degree the blood oxygen saturation.

OBJECTS AND SUMMARY OF THE INVENTION

The invention is therefore directed to overcome the risk of "false" positive and "false" negative events in medical devices equipped with means for detecting the respiratory disorders, and in particular in medical devices that are implanted.

The starting point of the present invention lies in the clinical observation by the inventor that, in response to the hypoxia generated by apneas or hypopneas and in the absence of a respiratory flow (i.e., not inflated lungs), the carotid chemo-receptors promote a vagotonic effect on the heart so that, according to the state of the sympathico-vagale balance, the apneas or hypopneas can induce a bradycardia. Then, at the end of the apneic or hypopneic episode, the ventilatory recovery which can follow a micro-waking up or a modification of the regulation of the $CO_2$ partial pressure in blood is accompanied almost systematically by a tachycardia under the effect of an increase of the sympathetic tonicity on the heart. This increase results from several factors such as consequences of a micro-waking up, detection of the hypoxia by the peripheral chemoreceptor, or co-activation of the neurons of the sympathetic cardiovascular nerve system by the breathing centers. Thus, the repetition of the apneas or the hypopneas confers on the heart rate a cyclic aspect with alternation of episodes of bradycardia/tachycardia which can be characteristic.

One aspect of the present invention is directed to a device that is an active medical device as defined in the directive 93/42/EEC of Jun. 14, 1993 of the Council of the European Communities, more preferably an "active implantable medical device" according to the directive 90/385/EEC of Jun. 20, 1990 of the Council of the European Communities, and even more particularly to a device such as a cardiac pacemaker, a defibrillator, a cardiovertor and/or a multisite device. This device includes, in a known manner, means for collecting (sensing) the heartbeat rate in at least one cavity of the heart, and means for evaluating a cardiac frequency value as a function of the collected rate.

In a manner characteristic of the invention, the means for analyzing the rate includes means for discriminating in the collected rate spontaneous events of a sinusal origin and evaluating the heart rate only as a function of sinusal spontaneous events, and for analyzing variations in time of the aforementioned heart rate to determine the presence of a sleep respiratory disorder according to these variations.

In a first embodiment, the means for analyzing the collected rate comprises means able to seek in the aforementioned variations cyclic profiles of episodes of bradycardia followed by episodes of tachycardia.

In a second embodiment, the means for analyzing the collected rate comprises means for determining, and advantageously also memorizing (storing) in a memory, an index of sinusal variability as a function of the aforesaid variations, and comparing this index to a predetermined threshold.

In another embodiment, if the device includes a physiological sensor that is able to deliver a signal that is a measurement of the respiratory activity of the patient, it is advantageously envisaged to include a means for correlating the indications of this physiological sensor with those of the aforesaid means for analyzing the collected rate.

DETAILED DESCRIPTION OF THE INVENTION

One now will describe in a more detailed way various embodiments for implementing the present invention with reference to the FIGURE annexed.

Figure 2:
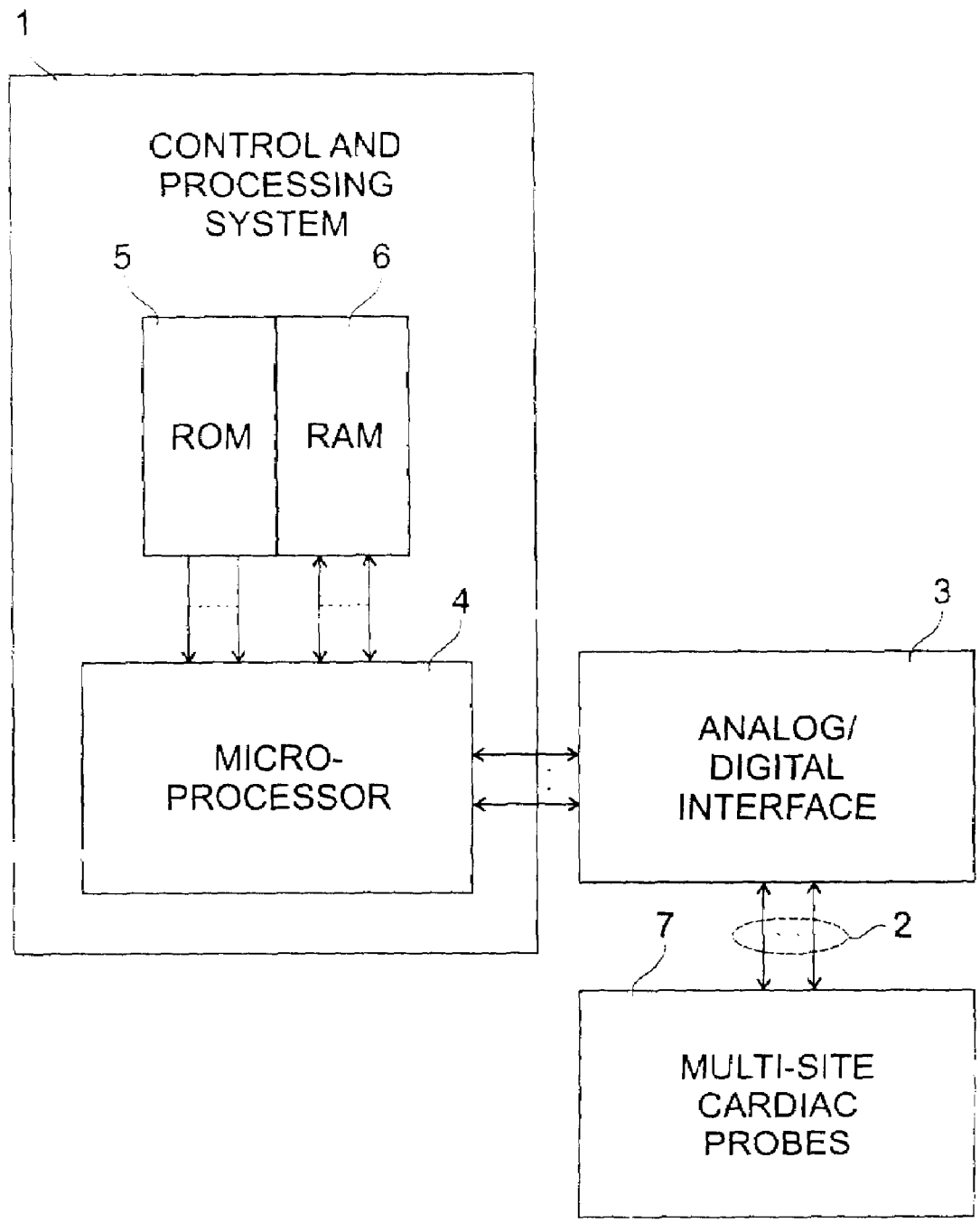
FIG. 2 illustrates schematically the general use of a typical pacemaker of multi-site type.

As indicated above, the present invention proposes to use an active implantable medical device to characterize respiratory episodes of sleep disorders by an analysis of the variations of the heart rate or the sinusal variability, so as to be able to carry out in an automatic and continuous way a detection and a diagnosis of the respiratory disorders presented by the patient. FIG. 2 illustrates in block form the typical structure of an implantable medical device of this type, including a control and processing system 1, multiple leads 2 connected to probes at cardiac sites, an analog/digitial interface for transferring the analog signals from the leads 2 to the microprocessor 4 and vice versa, a micro-processor 4 for the processing of instructions necessary in implementing the algorithm of the present invention. ROM 5 and RAM 6 for storing the software instructions and data for implementing the algorithm of the present invention, and cardiac probes 7 placed at multiple cardiac sites as is typical of known multi-site pacemakers. The diagnosis can be operated directly starting from the analysis of the heartbeat rate.

In the alternative or in complement, to improve the global specificity of this diagnosis, it is possible to use the analysis of the heartbeat rate carried out for the characterization of the sleep espiratory disorders, with additional information such as that delivered by another sensor, for example, a sensor of minute ventilation (MV sensor). In this latter case, the device of the invention can, for example, starting from a suspicion of apnea detected by the MV sensor, validate this episode from the heart rate analysis or, conversely, to suspect an apnea from the heartbeat rate evaluation, which will be validated by MV sensor indication.

Figure 1:
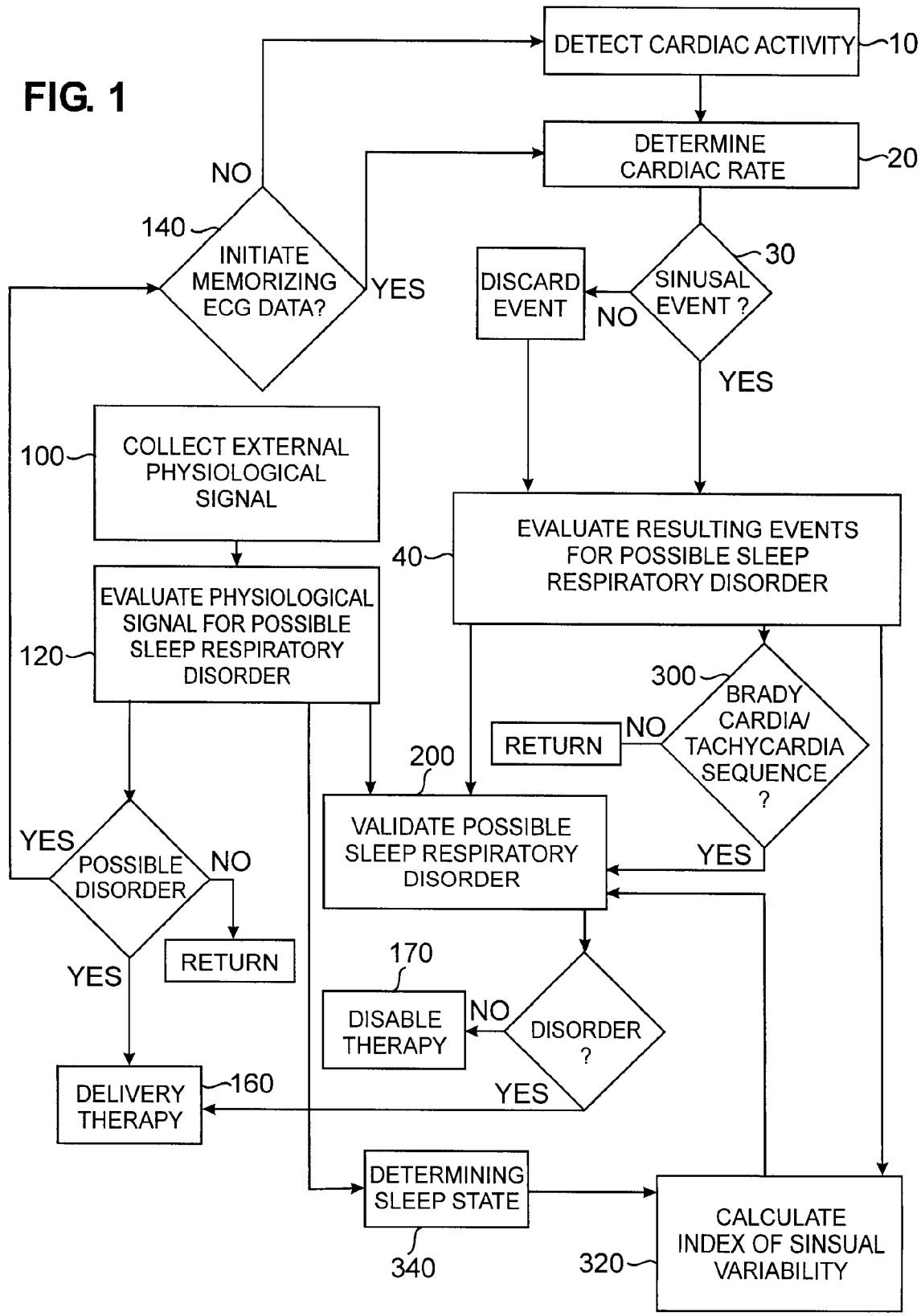
FIG. 1 illustrates a flow chart implementing an algorithm for detecting sleep disorders according to the present invention.

In addition to the detection of the sleep respiratory disorders (apnea and hypopneas), the study of the variations of the heartbeat rate makes it possible to characterize the reactivity of the sympathetic nerve system of the patient. This information in particular can, over the long term, serve to observe the effect of a medicamentous treatment such as the administration as a beta-blocker, or the evolution of a pathology such as a cardiac insufficiency. As shown in FIG. 1, in a general way, to achieve the above-mentioned goals, the device permanently monitors the cardiac signals (stage 10) so as to determine the sinusal frequency (stage 20). For that, the device can determine an interval PP (namely the interval between two spontaneous atrial waves) or an interval RR (namely the interval between two ventricular spontaneous QRS complexes), given that the variability of this interval PR cycle to cycle is regarded as negligible.

The device retains only the signals corresponding to a regular spontaneous activity (stage 30). For the analysis of the heartbeat rate, the device detects and eliminates extrasystoles and the atrial or ventricular salvos, which modify instantaneously the heart rate without necessarily being the consequence of variations finding their origin in the autonomous nervous system. The device also eliminates stimulated cardiac cycles, because in this case although the rate is a stable one it is an artificially imposed rate. After having selected only the significant PP or RR intervals, the device analyzes the cycles thus memorized to detect possible episodes of sleep respiratory disorder (stage 40). For that, two techniques can be implemented:
1. analysis of the profile of the variation of the heart rate, in order to identify cyclic profiles of bradycardia/tachycardia episodes (stage 300), or
2. analysis of the sinusal variability, this parameter reflecting the variations of the heart rate over the given period.

Characterization of an Episode of Apnea or of Hypopnea by Analysis of the Profile of the Heart Rate If the device is equipped with one or more sensors having an ouput signal that can be evaluated (stage 100) allowing one to suspect a sleep respiratory disorder (stage 120), for example, a sensor of minute ventilation operating by measurement of the transthoracic impedance, an intracardiac impedance or an PEA sensor (Peak Endocardial Acceleration), the device can evaluate the repercussion of this respiratory disorder on the heart rate, and this at several ends, in particular:
1. validation of a detection of a respiratory pathological episode (apnea or hypopnea, for example) (stage 200),
2. the characterization of the impact of the event on the heart rate (existence or not of an alternating bradycardia/tachycardia, amplitude and duration of the bradycardia and of the tachycardia) (stage 300), etc., and
3. the instantaneous trigger of a reaction of the apparatus (stage 140): memorizing of other information (for example, of an intracardiac ECG) or implementation of a therapy aiming at preventing possible new phases of bradycardia/tachycardia, in particular by maintaining a higher stimulation frequency (stage 160).

Thus, in the example where the device is equipped with a sensor of transthoracic impedance able to identify a sleep apnea, when this sensor detects an apnea, the device analyzes in the following way the profile of the heart rate.
a) taking into account n cardiac cycles preceding the detection of the apnea and the m cycles following this detection;
b) computing a variation cycle to cycle of a cardiac interval (PP or RR);
c) when the variation reaches a predetermined positive threshold, detection of the beginning of bradycardia;
d) when the variation changes its sign, detection of the beginning of tachycardia;
e) memorizing the duration of the bradycardia and of the minimum value of the heart rate;
f) when the variation is stabilized, detection of the end of the tachycardia;
g) memorizing the duration of the tachycardia and the maximum value of the heart rate;
h) if the detected and memorized characteristics of the bradycardia and of the tachycardia fulfill of predetermined criteria (e.g., duration, threshold of frequency, etc.), detection of the apnea episode is validated.

One will note that, to allow an analysis in real time, certain stages of calculation can be anticipated, for example, the precalculation of the cycle to cycle variation of the interval and the determination of the direction and the magnitude of this variation.

Characterization of the Respiratory Profile of the Patient by Analysis of Sinusal Variability In this embodiment, the sinusal variability is analyzed, alone or in complement of any other parameter, to determine the presence or the absence of a sleep respiratory disorder (stage 300). Starting from the recorded heartbeat rate data, an index of sinusal variability is calculated (stage 320), in the temporal field or in the frequency field. This calculation can be operated either internally within the implanted device, or by an external device that receives by telemetry information collected and recorded by the implanted device.

Calculation can be carried out for a determined time period and/or according to events detected by the implanted apparatus. For example, if the device is equipped with a means for detecting the sleep state of the patient (stage 340), the index of sinusal variability can be calculated separately for the awakening phase and the sleep phases. One will be able to refer in this respect to the United States Published Patent Application US2003/0163059, 030828 commonly assigned herewith to ELA Médical, which document is incorporated herein by reference in its entirety and describes an implanted device equipped with means for discriminating of the phases of awakening and sleep for a patient. Indeed, in the case of a healthy patient, the index varies little between day and night, unlike an apneic patient where this index significantly presents more large variations. If the index of sinusal variability of the night (i.e., the sleep phase) reaches a predetermined threshold, or if the night/day ratio of the indices reaches a predetermined threshold, one can conclude that sinusal variability is significantly high during the sleep phase. The threshold value will make it possible to discriminate the healthy patients from the patients presenting sleep respiratory disorders, or being likely to present such disorders.

Over time, the evolution of the sinusal variability index can be memorized, for example, calculated and memorized every 24 hours, alone or in complement to information delivered by other sensors. This can be done to evaluate the effectiveness of a treatment (for example, treatment of an obstructive apnea by institution of a continuous positive pressure) or the evolution of a sleep respiratory disorder (for example, related to a significant increase in weight). Many indices, in themselves known, can be selected to represent the sinusal variation.

One can use the following indices, calculated by analysis in the temporal field (time domain):

1. $PNN_{50}$ (Normal-to-Normal Percentage) which is the percentage of cycles whose variation cycle to cycle is higher than 50 ms,
2. RMSSD, which is the square root of the ratio between, on the one hand, the sum of the squares of the differences in duration of two consecutive cycles and, on the other hand, the total number of analyzed cycles, or
3. SDNN (Standard Deviation Normal-to-Normal), which is the standard deviation of the intervals of the cardiac cycles.

In the frequency field (domain) it is possible, for example, after a spectral analysis of the intervals of the cardiac cycles by a Fast Fourier Transformation (FFT) and the determination of the spectral bands, to calculate the ratio of the powers between the low frequencies (for example, over the range 0.02 Hz–0.15 Hz) and the high frequencies (for example, higher than 0.2 Hz).

For an application in real time, one preferably chooses an index of sinusal variability in the temporal field.

If, for example, the SDNN index is chosen, the characterization of an episode of apnea can then be operated in the following way:

1. First, periodically, the index of sinusal variability in the absence of suspicion of apnea or hypopnea is calculated so as to constitute a reference index. If the device is equipped with a means for detecting the sleep state of the patient, the index of reference is advantageously calculated separately for the phases of awakening and the phases of sleep. One can thus, for example, calculate SDNN over 30 cardiac cycles every 10 minutes (150 cardiac cycles), and memorize the average minimum and maximum values of SDNN to be used as reference indices.
2. Next, when an apnea or hypopnea one is suspected by another sensor (for example, a sensor of minute ventilation) (e.g., stages 100-120), the running SDNN is calculated over the n cycles preceding and m cycles following this detection, for example, the n=20 cycles preceding and the m=10 cycles following the detection of the suspicion of apnea or hypopnea.
3. Then, if the current SDNN is significantly higher than the reference SDNN, there is a validation of the detection of the episode of apnea or hypopnea of, for example, if the current SDNN is higher than x times the reference SDNN, or higher than x times the maximum value of the SDNN of reference.

In the case of a validation, a therapy can be delivered (stage 160) and in the opposite case delivery of a therapy may be disabled (stage 170).

Suitable devices for which the present invention has application include, for example, the active implantable medical devices available from Ela Médical, Montrouge France. These devices are microprocessor-based systems having circuits for receiving, conditioning and processing detected electrical signals, and that are capable of receiving software instructions by telemetry, storing them in memory, and then executing those instructions to perform the functions described above in implementing the present invention. The creation of suitable software instructions for controlling an implant to perform the aforementioned functions of the present invention are believed to be within the abilities of a person of ordinary skill in the art. The detection circuits used to detect the cardiac signals in the atrium and/or the ventricle, in the left and/or right chambers (or more than two chambers in the case of a multi-site device), are well known; any suitable design may be used. The circuits used to inject the currents to obtain the bioimpedance measurements are known as well from, for example, EP 1 116 497 and corresponding U.S. Pat. No. 6,604,002 B1 and EP 1 138 346 and corresponding U.S. Published Pat. Application 2001-0034540, which U.S. patent and published application are incorporated herein by reference, in their entirety and any suitable circuit to do so may be used. The activity sensor used and the determination of rest (sleep) phases might be taken from the devices disclosed in, for example, U.S. Pat. No. 5,722,996 and EP1317943 and its corresponding U.S. Published Patent Application 2002-10310689, which U.S. patent and published application are incorporated herein by reference.

The hemodynamic sensor can be in particular an endocardial acceleration sensor of the type PEA (Peak Endocardial Acceleration) as described, for example, in the EP-A 0 515 319 and its corresponding U.S. Pat. No. 5,304,208, EP-A 0 582 162 and its corresponding U.S. Pat. No. 5,454,838, or EP-A 0 655 260 and its corresponding U.S. Pat. No. 5,496, 351 (which are assigned to Sorin Biomedica Cardio SpA) and which U.S. patents are incorporated herein by reference in their entirety. A suitable commercial device for measuring heart acceleration is available from Sorin Biomedica Cardio SpA under the trade name Living CHF, and an electrode having an accelerometer at its tip also is available from Sorin under the trade name Best. The hemodynamic sensor can be also a sensor of endocardiac impedance, for example, a sensor of transvalvular bio-impedance, as described by the EP-A 1 116 497 and its corresponding U.S. Pat. No. 6,604,002, or of trans-septum bio-impedance, as described by the EP-A 1 138 346 and its corresponding published U.S. Patent Application US2001/0034540 A1 011029, both in the name of ELA Medical, which U.S. patent and publication are incorporated herein by reference in their entirety.

One skilled in the art will appreciate that the present invention can be practiced by other than the described embodiments, which are presented for purposes of illustration and not of limitation. Indeed, it should be understood that the drawing is illustrative of an embodiment of the invention, but that the invention can be practiced without having all of the functionality that is illustrated therein.

I claim:

1. An active implantable medical device comprising:

means for collecting a heartbeat rhythm in at least one heart cavity and implantable means for analyzing the collected heartbeat rhythm and evaluating a value of heart rate as a function of the collected rhythm, wherein the means for analyzing the collected heartbeat rhythm further comprises means for discriminating in said collected heartbeat rhythm spontaneous events of a sinusal origin;

means for evaluating the heartbeat rate as a function of said discriminated sinusal spontaneous events;

means for computing a variation in time of said heartbeat rate, wherein each variation comprises the difference in duration of a successive cardiac interval from a preceding cardiac interval; and means for determining from said variations a presence of a sleep respiratory disorder.

2. The device of claim 1, wherein the analyzing means further comprises means for determining an index of sinusal variability as a function of said variations, and means for comparing said index with a predetermined threshold.

3. The device of claim 2, further comprising means for memorizing said determined index of sinusal variability.

4. The device of claim 1, further comprising a physiological sensor having an output signal corresponding to the respiratory activity of the patient, and means for correlating said physiological sensor output signal with an output signal of the means for analyzing the collected heartbeat rhythm.

5. The device of claim 4 wherein the correlating means further comprises means for confirming an apnea condition as a function of said correlation.

6. The device of claim 1, wherein said analyzing means further comprises means for processing said aforementioned variations and determining therefrom cyclic profiles of episodes of bradycardia followed by episodes of tachycardia.

* * * * *